United States Patent [19]

McNaughton et al.

[11] Patent Number: 4,474,572
[45] Date of Patent: Oct. 2, 1984

[54] IMPLANTING DEVICE AND IMPLANT MAGAZINE

[75] Inventors: Allen D. McNaughton, Mountain View; Stephen B. Albert, Redwood City; Gerard A. Furbershaw, Santa Clara, all of Calif.

[73] Assignee: Syntex (U.S.A.) Inc., Palo Alto, Calif.

[21] Appl. No.: 491,691

[22] Filed: May 5, 1983

Related U.S. Application Data

[62] Division of Ser. No. 306,850, Sep. 29, 1981, Pat. No. 4,400,170.

[51] Int. Cl.$^3$ ............................................. A61M 5/00
[52] U.S. Cl. ...................................... 604/61; 604/63; 128/330
[58] Field of Search ............................. 604/57, 59–64; 128/330; 227/19, DIG. 1

[56] References Cited

U.S. PATENT DOCUMENTS

| | | | |
|---|---|---|---|
| 3,307,389 | 3/1967 | Rose et al. | 227/19 |
| 4,077,406 | 3/1978 | Sandhage et al. | 604/61 |
| 4,105,030 | 8/1978 | Kercso | 604/61 X |
| 4,223,674 | 9/1980 | Fluent et al. | 604/61 X |

Primary Examiner—C. Fred Rosenbaum
Assistant Examiner—Michelle N. Lester
Attorney, Agent, or Firm—John A. Dhuey; Joseph I. Hirsch

[57] ABSTRACT

An implanting device for implanting pellets and like subcutaneously or intramuscularly in animals is described which utilizes means for indexing an implant magazine having a plurality of pellet-containing stations therein and means for automatically retracting a needle from about an implant charge to deposit the pellets in an animal. The implant magazine is indexed for sequential applications automatically as the retraction mechanism is cocked. Additionally, means for automatically ejecting a spent or empty implant cartridge are provided to prevent false deposition of implants. An implant cartridge having open channels containing implants can be utilized with the implanting device, the channels having means thereon for increasing the size of the channel during the implanting step to substantially eliminate the crushing or breaking of pellets as they are expelled from the cartridge. Alignment and stabilization means for the implant magazine and the implanting device also are provided.

22 Claims, 20 Drawing Figures

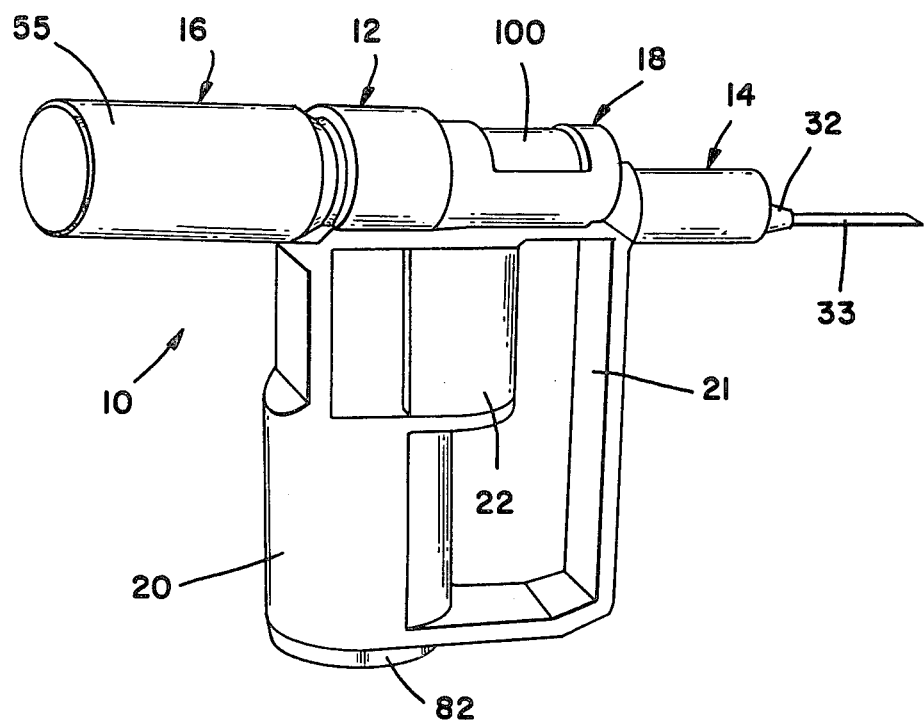
FIG_1
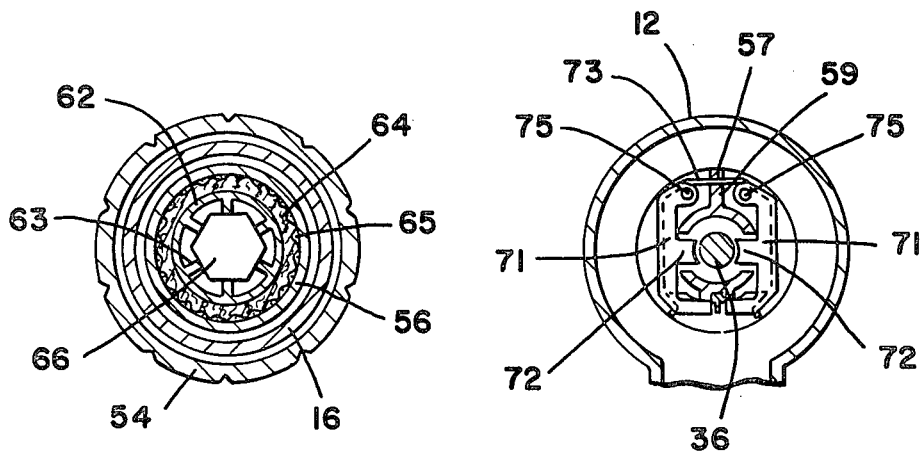
FIG_3  FIG_4

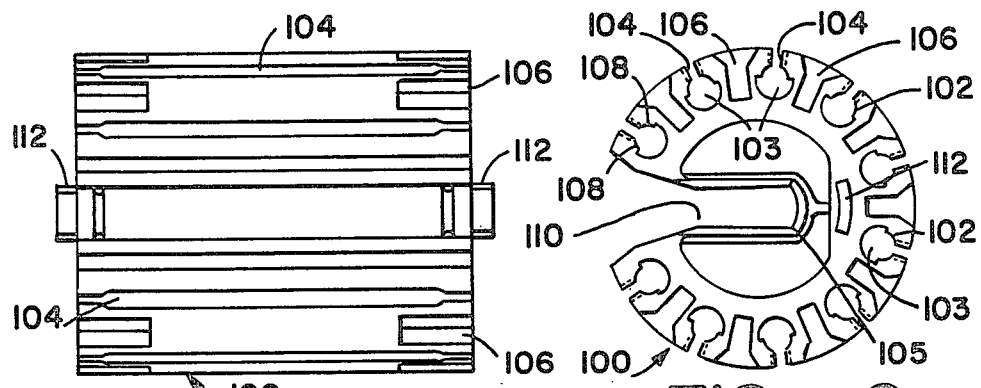
FIG_5  FIG_6
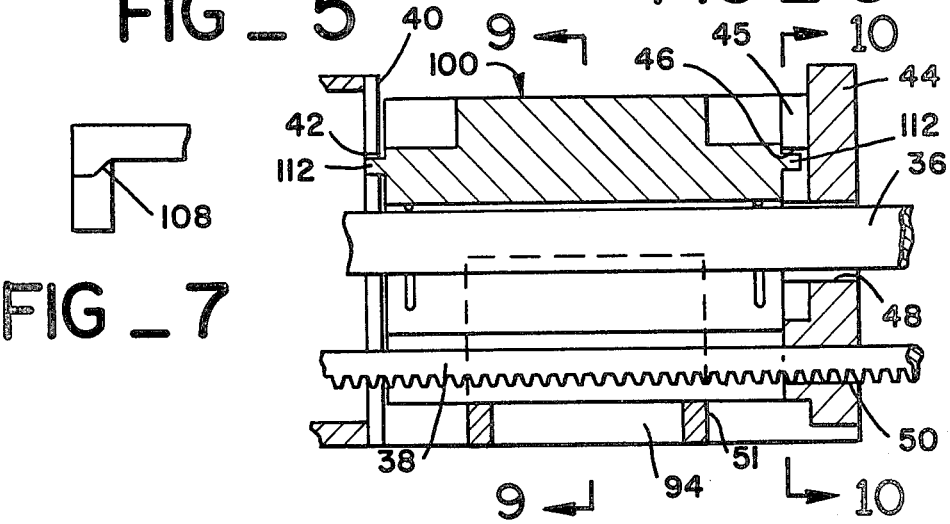
FIG_7  FIG_8
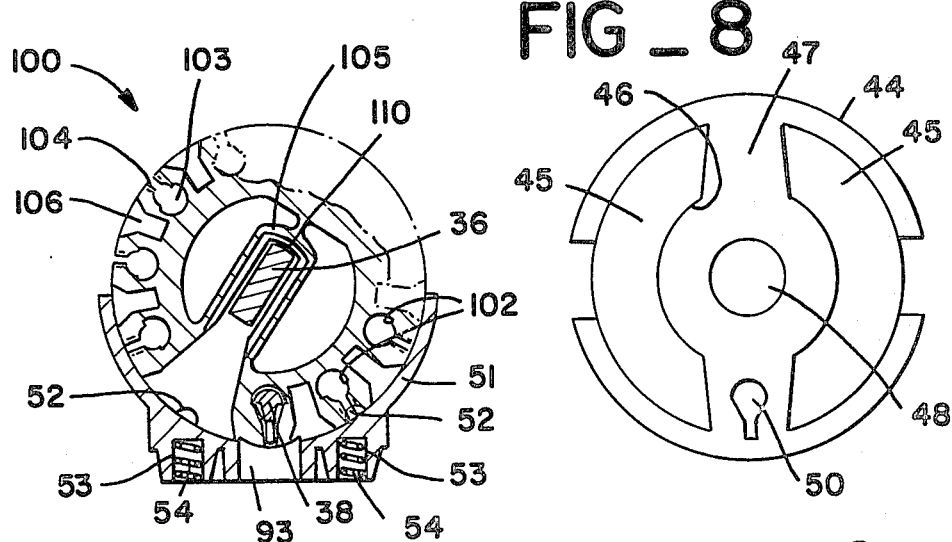
FIG_9  FIG_10

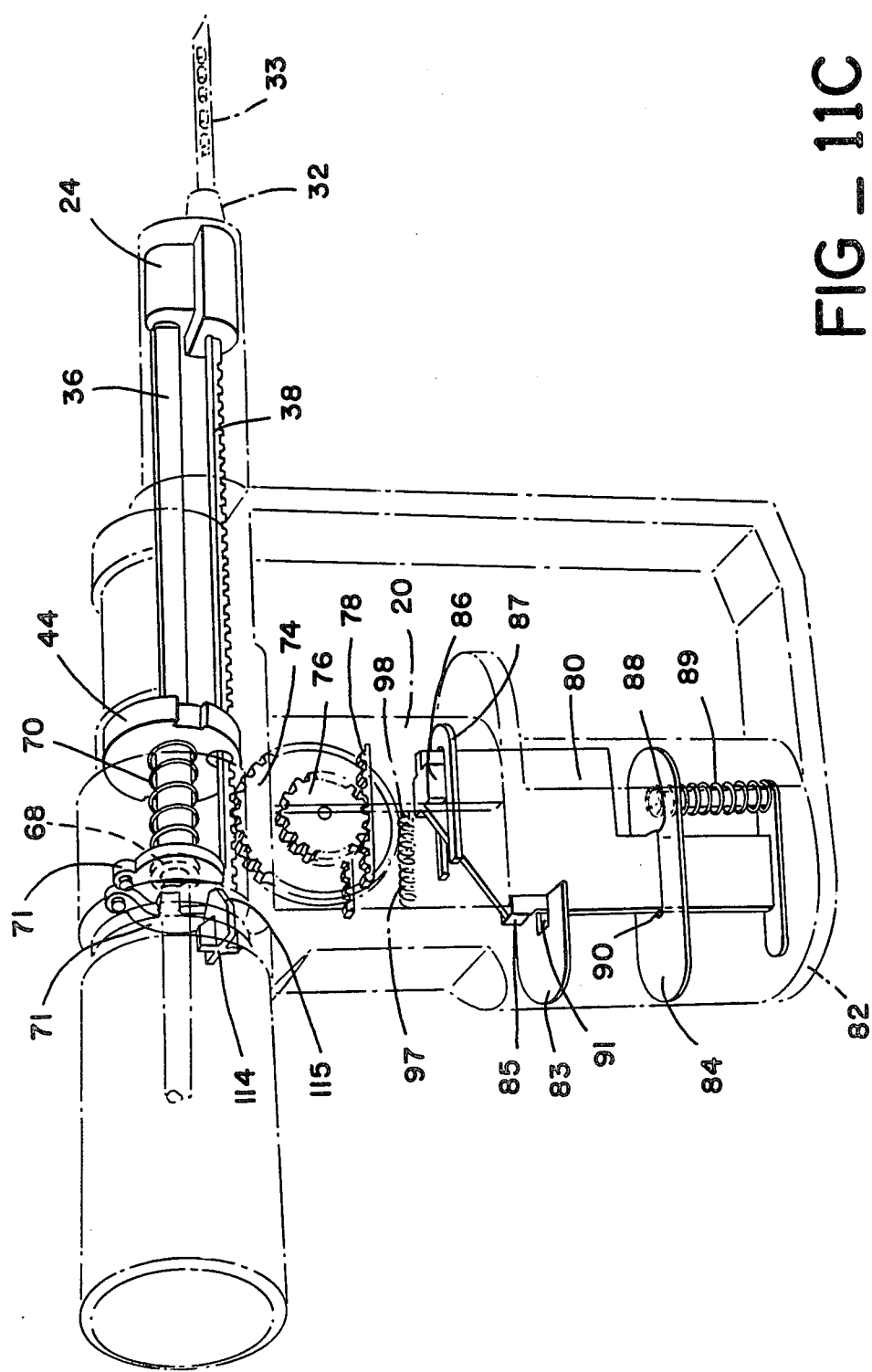
FIG_11C

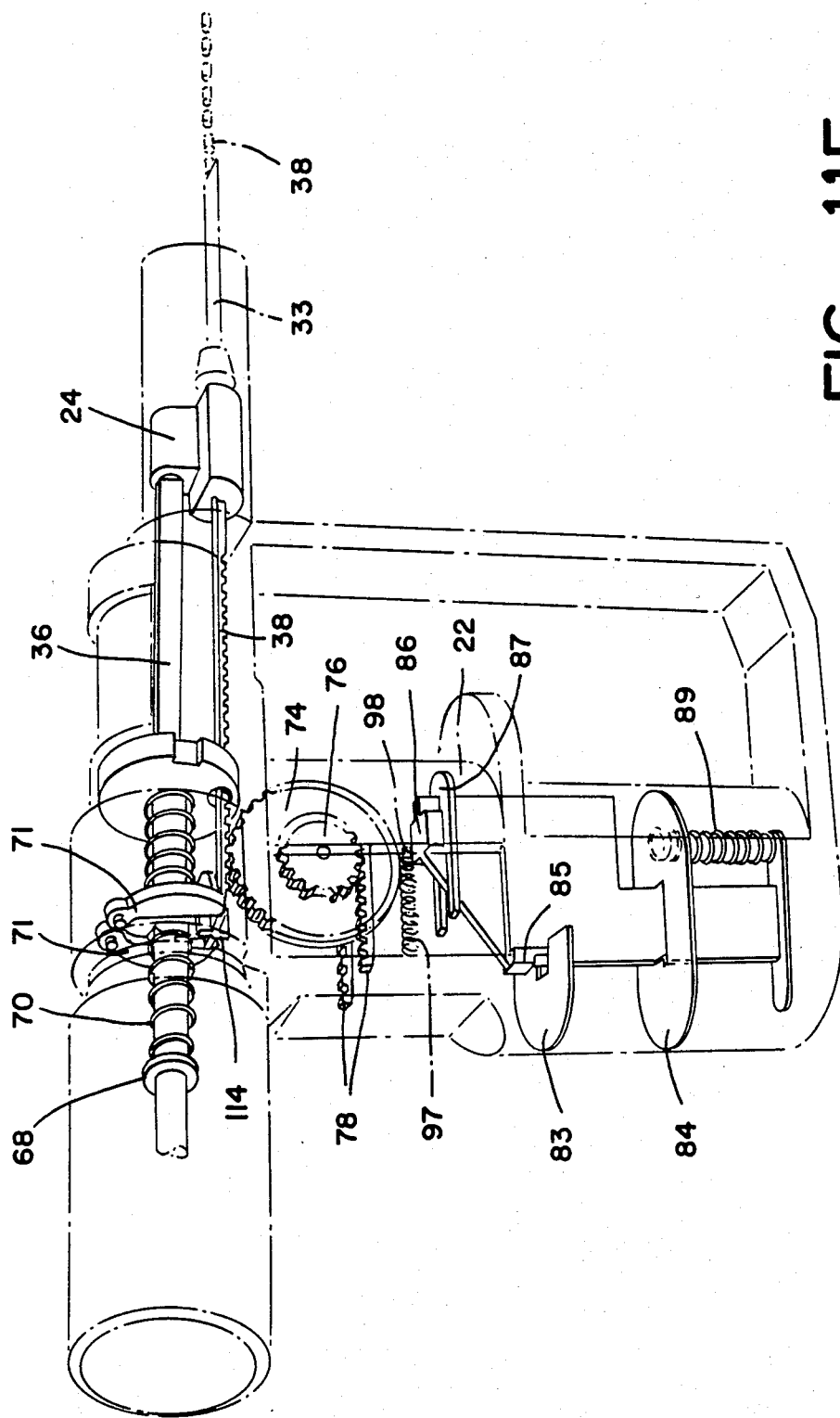
FIG_11E

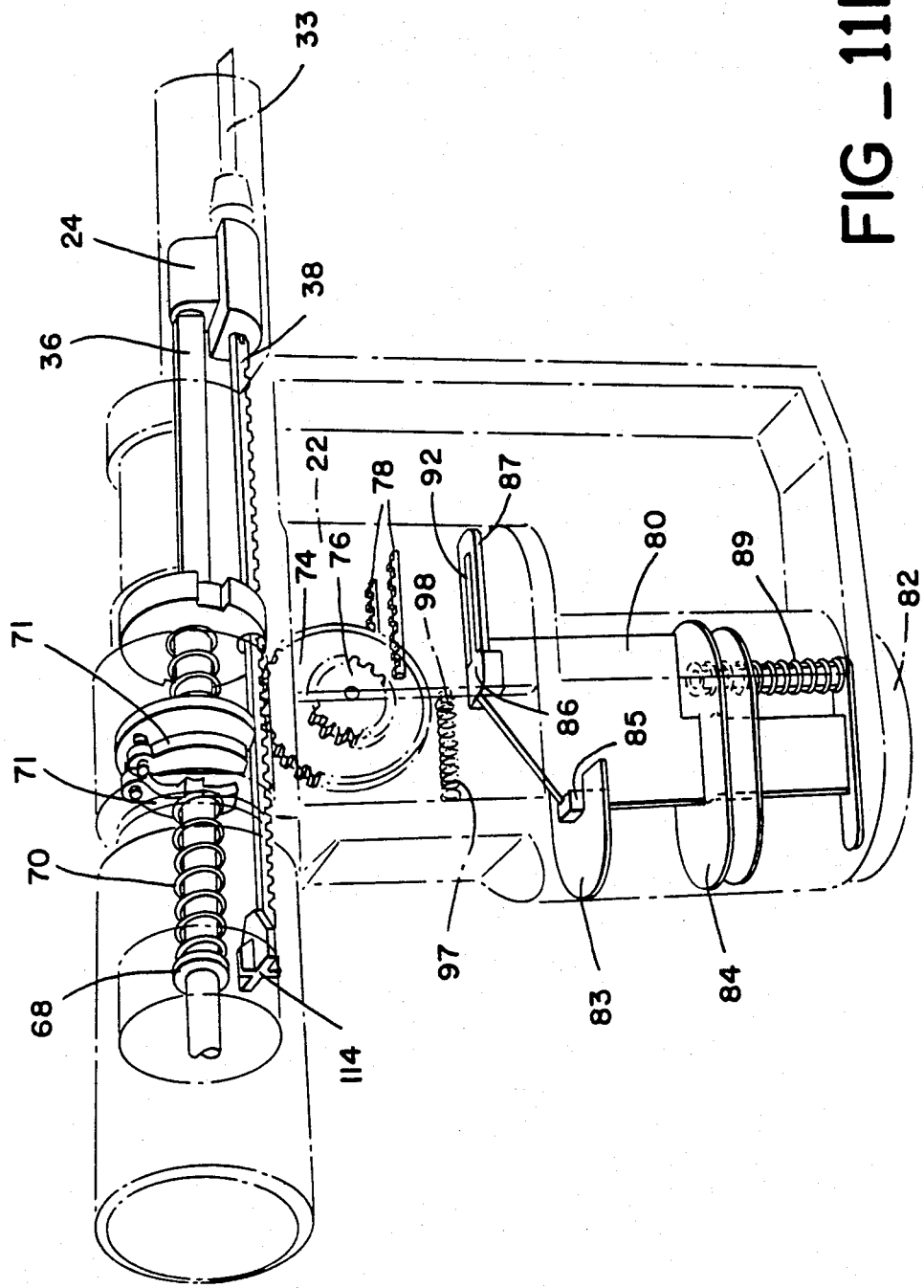
FIG_11F

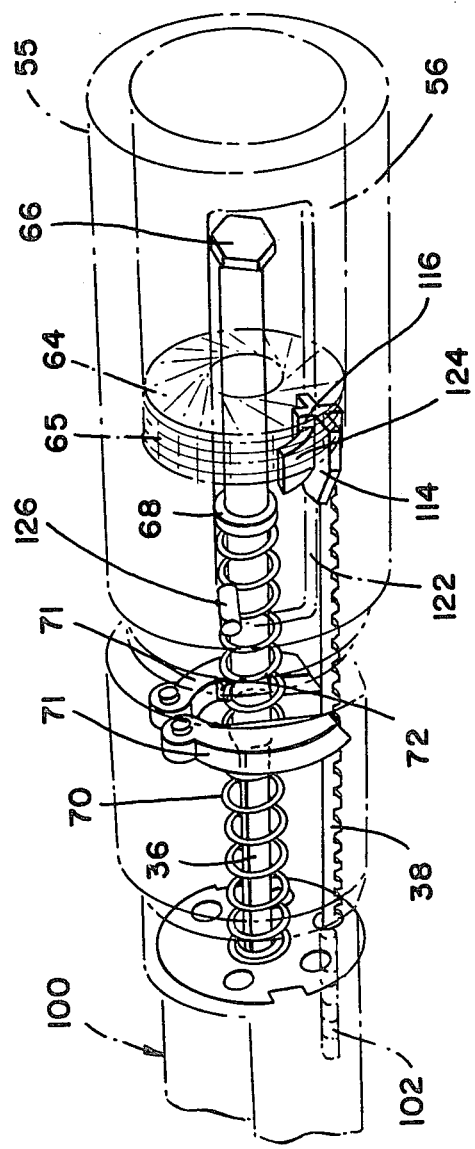
FIG_12A
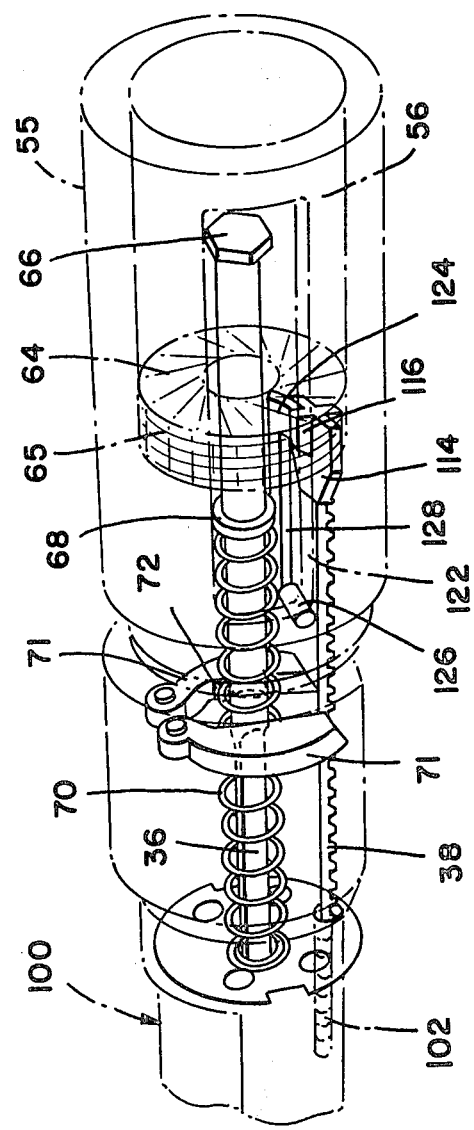
FIG_12B

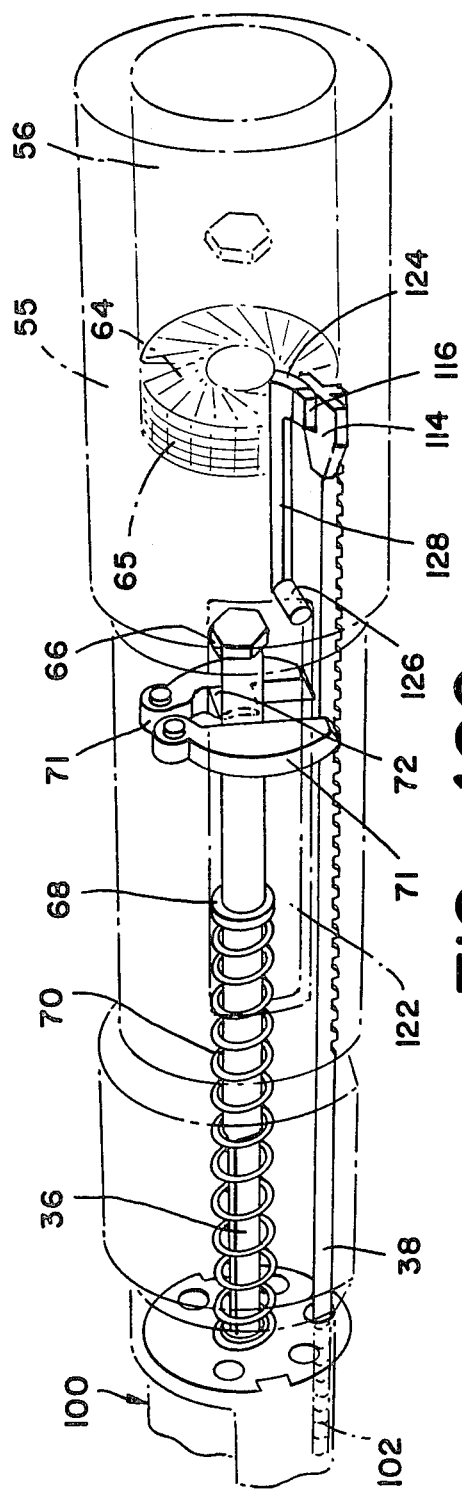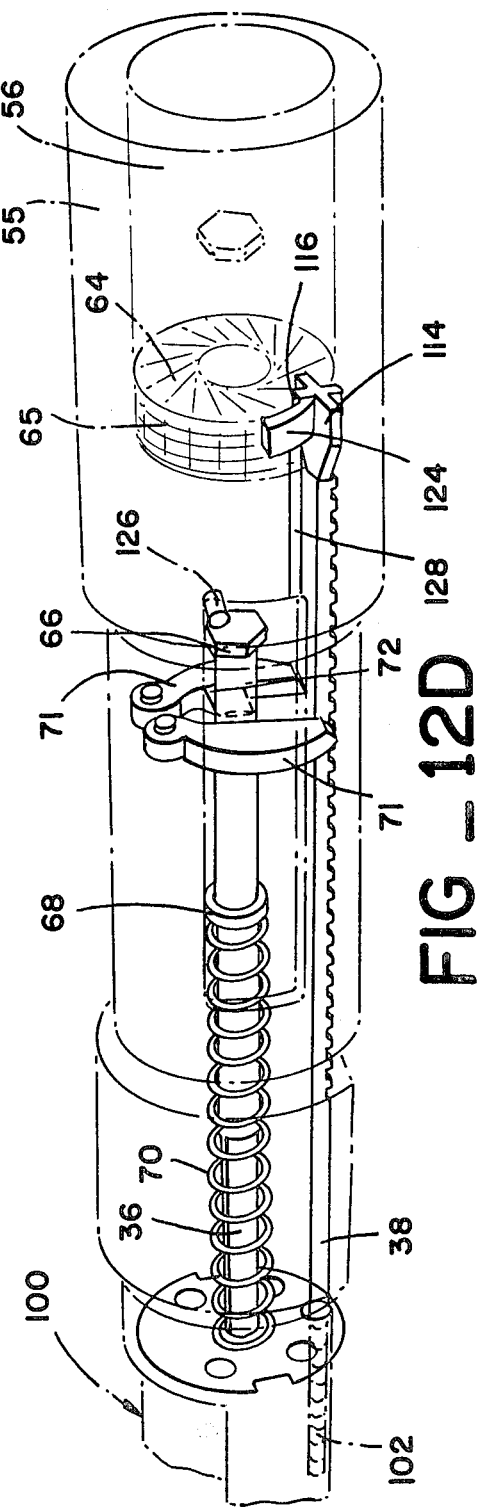

IMPLANTING DEVICE AND IMPLANT MAGAZINE

This is a division of application Ser. No. 306,850, filed Sept. 29, 1981 now U.S. Pat. No. 4,400,170.

BACKGROUND OF THE INVENTION

1. Field of the Invention

The present invention relates to implanting devices for implanting pellets or the like, e.g. growth promotant implants, subcutaneously or intramuscularly in animals. In particular, the present invention relates to those devices having a retractable needle and a mechanism for sequencing an implant magazine having a plurality of pellet-containing stations therein for sequential administration of the implant doses. Additionally, the invention relates to an implant magazine having a plurality of pellet-containing stations therein which has means for facilitating the ejection of pellets from the implant magazine and substantially eliminating or preventing breakage and crushing of the implant pellets.

2. State of the Art

Numerous implanting instruments have been described in the art. The following patents are considered representative examples thereof: U.S. Pat. Nos. 2,632,444; 2,883,984; 3,058,465; 3,088,207; 3,402,712; 3,520,299; 3,538,916; 3,669,104; 4,077,406; 4,105,030; 4,154,239; 3,774,607; 4,223,674; Canadian Pat. No. 455,838; and Australian Pat. Nos. 223,184; 228,022; 253,175; and 288,070. Additional patents relating to implant cartridges and other magazines generally are U.S. Pat. Nos. 202,613; 1,559,825; 2,493,922; 2,587,687; 2,601,852; 3,477,419; 3,913,553; and 3,729,853.

Many implant dosage forms are relatively fragile and have a tendency to break or crush when forced out from the implant magazine into and through the needle into animal tissue. Relatively recently, devices having a retractable needle which obviates the necessity of pushing pellets from the implanter into the tissue have been developed. For example, U.S. Pat. Nos. 4,223,674 (Fluent et al) and 4,105,030 (Kercso) have described devices having a retractable needle which is drawn rearwardly from about the implant pellets to permit the pellets to remain in the animal tissue. However, there remains the problem of expelling the implant pellets from the implant magazine itself into the needle. During that step of the implanting procedure, there is a tendency for pellets to break or crush. Additionally, it is not generally desirable to have the implant pellets freely moveable within the pellet containing stations of the implant cartridge since there is a tendency for the pellets to drop out during handling of the implant magazine such as, for example, when the implant magazine would be loaded into the implanting device. Furthermore, each of those devices utilizes a multidose magazine which requires manual indexing of the implant magazine for each sequential application of an implant to an animal. Such manual indexing is unsatisfactory in many applications such as feedlot usage where large numbers of animals are implanted during one operation. Additionally, failure to manually index the cartridge prior to implantation would result in a false implant. Accordingly, there is a need for automatically indexing the cartridge prior to the sequential injection of subsequent animals.

SUMMARY OF THE INVENTION

The present invention has several aspects. In one aspect, the invention relates to an implant magazine comprising a generally cylindrical body having a plurality of longitudinally extending open channels about the circumference thereof, each of the channels having means associated therewith for retaining implants within the channels prior to implantation and for increasing the size of the channel to release the implants during the implantation step, thereby substantially eliminating crushing or breaking of the implants. In that aspect, the invention is particularly characterized by means on the inner surface of the open channels adapted to be contacted by the implants to increase the cross-sectional area of the channel during the implantation step, thereby partially releasing the implants disposed therein. Additionally, in a presently desired embodiment, the releasing means includes a cavity disposed between each of the open channels on the circumference of the implant body which permits additional flexing of the open channels in a facile manner to permit gentle release of the implant pellets from the implant magazine.

In another aspect, the invention comprises a device for implanting pellets and the like into an animal comprising a needle support means moveable between a first position and a second position, means for supporting an implant magazine having a plurality of pellet-containing stations therein, means for depositing a pellet from an implant magazine into the needle support means, means for aligning a pellet-containing station of the implant magazine with the depositing means and the needle support means, and means for moving the needle support means between the first position and the second position. The implanting device can further include means for automatically ejecting an implant magazine from the support means upon the emptying of the pellet-containing stations of the implant magazine. The invention in that aspect is characterized by the alignment means including a rotatable shaft for engaging an implant magazine mounted on the implanting device, the rotatable shaft being operatively coupled to a one-way clutch to permit rotation of the implant magazine and the rotatable shaft in only a single direction.

In still another aspect, the present invention is directed to a device for implanting pellets and the like into an animal comprising a housing having a forward end and a rearward end, needle support means mounted on the housing adjacent the forward end thereof, the needle support means being moveable between a first position and a second position, means on the housing for supporting an implant magazine having a plurality of pellet-containing stations therein, an implant rod supported within the housing and moveable between a third position and a fourth position, first means for moving the implant rod between the third and fourth positions, a needle retraction rod supported on the housing, the needle retraction rod being coupled to the needle support means and adapted to engage an implant magazine supported on the housing, means on the housing for rotating the needle retraction rod to align a pellet-containing station of an implant magazine with the implant rod, and second means for moving the needle support means between the first and second position. That aspect of the invention also can include means associated with the housing for ejecting an implant magazine from the support means on the housing when the implant magazine has been emptied.

In still another aspect, the present invention is directed to an implanting device of the above-described type including safety means associated with the implanting device for releasably maintaining an implant rod in a fixed position to prevent inadvertent release of the pellets from the implanting instrument.

In yet a further aspect of the invention, the invention is directed to an implant device of the type described above in combination with an implant magazine supported on the implant device, the implant magazine having guide means thereon for interacting with a portion of the implanting device to maintain the implant magazine in a fixed position during the implanting of an implant into an animal. That aspect of the invention is particularly characterized by the guide means being a longitudinal slot in each of the open channels of the pellet-containing stations of the implant magazine and an enlargement, such as an enlarged tooth, on the implanting rod which engages and slides within the slot formed on the implant magazine.

DETAILED DESCRIPTION OF THE DRAWINGS

FIG. 1 is a perspective view of the implanting instrument of the present invention;

FIG. 3 is a sectional view along line 3—3 of FIG. 2;

FIG. 4 is a sectional view along line 4—4 of FIG. 2;

FIG. 5 is a side-elevational view of an implant magazine utilized with the implanting device of the present invention;

FIG. 6 is an end view of the implanting magazine of FIG. 5;

FIG. 7 is a detail view of an end of a channel of the implant magazine;

FIG. 8 is an elevational view, partly in section, of the implant magazine supported within the implant device;

FIG. 9 is a sectional view along line 9—9 of FIG. 8;

FIG. 10 is a front, end view of the spring plate;

Figure 2:
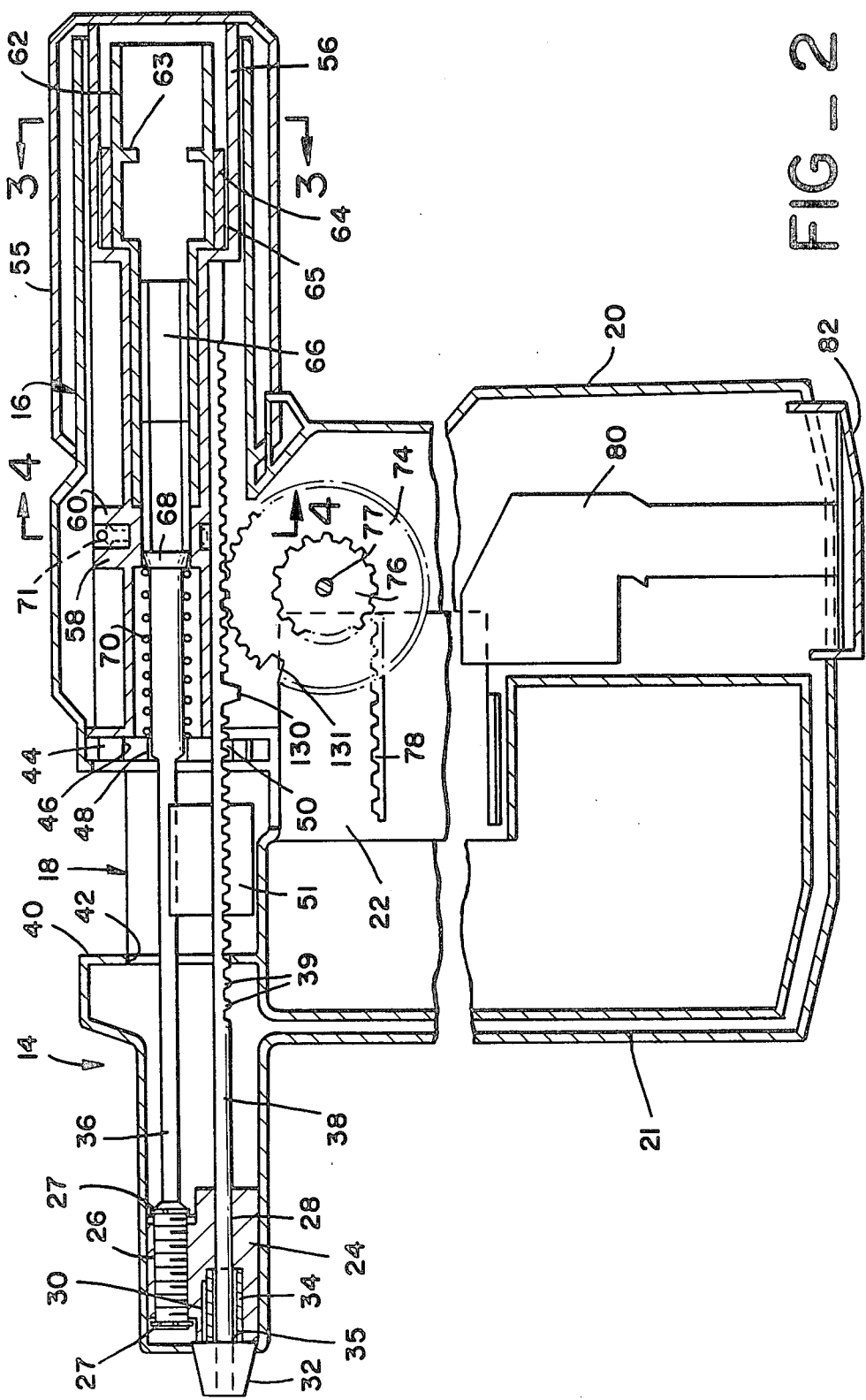
FIG. 2 is a cross-sectional view of the implanting device.

FIGS. 11A-F are views showing certain internal aspects of the present invention; and FIGS. 12A-D are views showing the cocking mechanism of the present invention.

DETAILED DESCRIPTION OF THE INVENTION

With reference to FIG. 1, the implanting device 10 of the present invention comprises a housing 12 having a forward portion 14, a rearward portion 16 and an intermediate portion 18. A hand grip 20 having a handle 21 and a trigger 22 is attached to housing 12. Disposed about the rearward portion 16 of housing 12 is a cocking grip 55. A safety button 82 is disposed at the bottom end of grip 20, the function of which will be described hereinafter. An implant magazine 100 is supported within housing 12 and a needle support 32 and needle 33 are located within and adjacent to the forward portion 14 thereof.

As can be seen most clearly from FIG. 2, the implanting device 10 has a bridge 24 located within housing 12 at the forward portion 14 thereof. Bridge 24 is provided with an upper bore 26 which receives a needle retraction rod 36 therein. Needle retraction rod 36 is axially fixed within bore 26 by means of C-clips 27 attached to needle retraction rod 36 at each end of bore 26. Needle retraction rod 36 is free to rotate within bore 26 but cannot slide axially either forwardly or rearwardly. A lower bore 28 is provided in bridge 24 to receive at various stages of the implanting procedure implant pellets or implant rod 38. Bore 28 is appropriately sized so that implant rod 38 can slide forwardly and rearwardly therethrough to deposit pellets into the animal being implanted. A counterbore 30 is provided at the forwardmost end of bridge 24 to receive a needle support 32 to which a needle 33 can be attached. Typically, counterbore 30 is threaded to receive a mating threaded connection on needle support 32. A retaining means such as an insert 34 having flexible members 35 can be located within lower bore 28 to retain implant pellets within bridge 24 prior to implantation into an animal. When implant pellets are ejected from bridge 24 by implant rod 38, members 35 flex outwardly to permit the pellets to pass into needle 33.

The intermediate portion 18 of housing 12 is provided with an inner face 40 having a surface 42 thereon forming an annular groove which is adapted to receive a portion of implant magazine 100 as will be described hereinafter. The other end of intermediate portion 18 is adapted to receive a spring plate 44 which is fastened thereto. Spring plate 44 is provided with a pair of semicircular lugs 45, as can be seen most clearly in FIG. 10, which create a surface 46 which is adapted to contact a portion of implant magazine 100. That feature of spring plate 44 will be described more fully below. A centrally located bore 48 is provided through spring plate 44 to slidably receive needle retraction rod 36. A bore 50 is provided at the lower portion of spring plate 44 to receive implant rod 38. The lower portion of bore 50 assumes a substantially retangular cross-sectional configuration to permit the rack gear 36 formed on the bottom surface of implant rod 38 to pass therethrough.

At the bottom of intermediate portion 18 of housing 12 is provided an ejector cradle 51 which supports implant magazine 100. That feature of the invention can be seen most clearly from FIGS. 2, 8 and 9. The ejector cradle 51 has a generally semicircular cross-section which provides a surface complementary to cylindrical implant magazine 100 which is retained thereon. Nubs 52 are provided on the surface of ejector cradle 51 to engage slots 104 of implant magazine 100 and provide a stabilization and indexing mechanism therefor. The bottom portion of ejector cradle 51 is provided with a pair of vertical bores 53 which are adapted to receive springs 54 which bias ejector cradle 51 upwardly in housing 12. When implant magazine 100 is oriented such that portions thereof do not contact surfaces 42 and 46, and when magazine 100 is not restrained by needle retraction rod 36, ejector cradle 51 will force implant magazine 100 upwardly out from intermediate portion 18 of housing 12. That feature of the invention will also be described more fully below.

The rearward portion 16 of housing 12 is surrounded by a cocking grip 55. Cocking grip 55 is attached at its rearward end thereof to a concentrically arranged guide tube 56. Guide tube 56 is substantially cylindrical and is provided with a pair of retaining walls 58 and 60. A pair of sears 71, as can be seen most clearly in FIG. 4 and FIGS. 11A-F, are retained between retaining walls 58 and 60. A vertical rib 59 is provided on the top surface of guide tube 56 between retaining walls 58 and 60. A hole 57 is formed in rib 59 to receive a spring 73 which biases sears 71 to their closed position. Concentrically located within guide tube 56 is a clutch tube 62 having a series of support vanes 63 formed on the inner surface thereof near its rearward end for contacting and engaging end 66 of needle retraction rod 36 when needle retraction rod 36 is in its retracted position. The end 66 of needle retraction rod 36 is provided with a hexagonally-shaped cross-section to key it into clutch tube 62 which has an inner hexagonally-shaped surface in the forward end thereof complementary with the outer surface of end 66 of needle retraction rod 36.

As can best be seen from FIG. 3, the outer surface of clutch tube 62 is provided with a fiber mat 64 and the inner surface of guide tube 56 is provided with a screen 65, elements 64 and 65 comprising a fiber clutch, which permits rotation freely between clutch tube 62 and guide tube 56 in one rotational direction but provides for simultaneous rotation of clutch tube 62 and guide tube 56 in the opposite rotational direction. Such fiber-type clutches are well known in the art and other one-way clutch mechanisms could be used as well. For example, a wrapped spring clutch such as described in *Machine Design* (Mechanical Drives Reference Issue), page 43, June 18, 1981, can be used. With that type of mechanism, one end of the spring is fixed to guide tube 56 and the spring is wrapped about clutch tube 62. Rotation of guide tube 56 in one direction tightens the spring and causes clutch tube 62 to rotate, whereas rotation in the opposite direction loosens the spring and clutch tube 62 does not rotate. Forward of the hexagonally-shaped end 66 of needle retraction rod 36 is provided a hub 68 formed on the outer circumference of needle retraction rod 36. Hub 68 is adapted to restrain a spring 70 between it and spring plate 44. The function of spring 70 is to retract needle support 32 and a needle 33 attached thereto from a first position at which the needle is extended forwardly from the forward portion 14 of housing 12 to a second position at which the needle 33 is adjacent the front end of housing 12 and bridge 24 is adjacent magazine 100.

When spring 70 is in its compressed condition, movement of hub 68 is restrained by the action of sears 71. Upon spreading of sears 71 by a mechanism which will be described later, hub 68 is released from engagement with sears 71 and spring 70 operates to propel needle retraction rod 36 rearwardly in housing 12 and retract needle support 32 and a needle 33 attached thereto from its first extended position to its second retracted position. As can be seen best from FIG. 4, sears 71 are provided with inwardly extending tabs 72 which are adapted to engage hub 68. A pair of posts 75 is provided on each of sears 71 and are adapted to engage a corresponding slot in guide tube 56. A spring 73, generally horseshoe-shaped, is disposed through a hole 57 formed in the top of guide tube 56 and retains sears 71 in a compressed configuration until they are spread by the mechanism to be described hereinafter.

The actuation mechanism for implanting a pellet from implanting device 10 is shown generally in FIG. 2. A gear train composed of a large spur gear 74 and a smaller spur gear 76 integrally joined therewith is supported about a pivot pin 77 on housing 12. Small spur gear 76 is configured and arranged to intermesh with a rack gear 78 provided on the inner surface of trigger 22. The gear teeth on large spur gear 74 are configured and arranged to intermesh with the rack gear 39 formed on the bottom surface of implant rod 38. When trigger 22 is forced rearwardly toward the end of housing 12, rack gear 78 causes small spur gear 76 and large gear 74 to turn in a counterclockwise direction, as shown in FIG. 2, which moves implant rod 38 forwardly within housing 12. That motion then expels pellets from bridge 24 outwardly through needle support 32 into a needle 33 attached thereto for subsequent implantation into an animal. A safety plate 80 is provided within grip 20 and is actuated by a safety button 82 to prevent inadvertent movement of trigger 22 in its rearward direction.

With particular reference to FIGS. 5-9, the implant magazine of the present invention comprises a generally cylindrical body having a plurality of pellet containing stations 102 disposed about the circumference thereof. Pellet stations 102 are formed with bottom chambers 103 having a substantially cylindrical configuration and those chambers open to the outer surface of implant magazine 100 through a plurality of slots 104 extending longitudinally the length of implant magazine 100. At each end of chambers 103 are provided a pair of ramp-like surfaces 108 which facilitate removal of the implant pellets from the chambers 103. Additionally, a plurality of relief volumes or cavities 106 are provided at each end of implant magazine 100 between chambers 103. Ramps 108 are adapted to be contacted by the pellets as they are ejected from chambers 103, thereby spreading apart the slots 104 and increasing the cross-sectional area of chambers 103 in an amount sufficient to permit easy expulsion of pellet implants contained therein. Because chambers 103 and slots 104 constitute open channels about the circumference of implant magazine 100, the material between adjacent channels and slots 104 can move slightly under the force of the pellets being ejected by implant rod 38. While the yielding of the material between slots 104 and chambers 103 is possible without the provision of relief cavities 106, the relief cavities 106 do facilitate that degree of yielding, particularly when the implant magazine is formed of somewhat rigid material, which is advantageous to express the pellets from the pellet stations 102 and substantially eliminate the breaking or crushing of the pellets as they are expelled from the implant magazine.

If desired, relief cavities 106 can extend the length of implant magazine 100 so as to provide additional channels to facilitate yielding of the walls defining chambers 103 and slots 104.

A large central mounting slot 110 defined by surface 105 is provided in implant magazine 100 and extends from the outer surface thereof to a position past the central axis of implant magazine 100. Slot 110 is adapted to fit over and about needle retraction rod 36. At each end of implant magazine 100 is provided a tab 112. One tab 112 is adapted to be retained beneath lugs 45 formed in spring plate 44 such that the implant magazine 100 is retained by surface 46 of lugs 45. At the other end of implant magazine 100, the other tab 112 contacts and is retained by surface 42 formed in the inner face of intermediate portion 18 of housing 12. In order to mount implant magazine 100 within implant device 10, it is only necessary to position slot 110 vertically with respect to housing 12 and slide implant magazine 100 and slot 110 downwardly about needle retraction rod 36. During that process one of tabs 112 slides downwardly through slot 47 formed between lugs 45 of spring plate 44 and the other of tabs 112 slides downwardly in a corresponding slot provided in inner face 40 of intermediate portion 18 of housing 12.

After implant magazine 100 has been inserted over and about needle retraction rod 36, it is given a small clockwise turn to position tabs 112 below surface 46 of lugs 45 on spring plate 44. The other tab 112 correspondingly becomes positioned beneath surface 42 formed on the inner face 40 of housing 12. At that position, the upward forces exerted by springs 54 on ejector plate 51 cannot force implant magazine 100 upwardly since it is restrained by the action of tabs 112 as described previously. Thus, implant magazine 100 is restrained within intermediate portion 18 of housing 12 for subsequent implants to an animal. As implant magazine 100 rotates within intermediate portion 18 for subsequent implantations, tabs 112 are restrained by surfaces 46 and 42 as described previously during the first and last quarter of the implantation cycle. During other portions of the implantation cycle, implant magazine 100 is restrained by needle retraction rod 36. When tabs 112 approach groove 47 in spring plate 44 at an approximately half-cycle of implantation, a portion of surface 105 of implant magazine 100 is held below needle retraction rod 36, which prevents the upward ejection of implant magazine 100. Continued rotation of implant magazine 100 then displaces tabs 112 to a position at which they are again restrained by surfaces 42 and 46.

After an implantation cycle has been completed with implant magazine 100, tabs 112 are outside of engagement with surfaces 42 and 46, and surface 105 is positioned at the top of and about needle retraction rod 36 such that the upward forces created by springs 54 in ejection cradle 51 force ejection cradle 51 upwardly and implant magazine 100 out of intermediate portion 18 of housing 12. Thus, implant magazine 100 is automatically ejected from housing 12 after the completion of an implantation cycle at which time the implant magazine is empty. The implant magazine 100 can then be easily removed by pulling upwardly thereon to slide it off of engagement with needle retraction rod 36 and a fresh, full implant magazine 100 can again be reinserted upon needle retraction rod 36 and turned clockwise to position tabs 12 under surfaces 42 and 46 for a subsequent implantation procedure. As an added advantage, when ejection cradle 51 is in a raised position, subsequent cocking of the injection device is not possible since implant rod 38 will strike the end of ejection cradle 51 during the cocking operation. Thus, the possibility of a false implant is eliminated.

The provision of open channels in the implant magazine of this invention is particularly advantageous in that it permits yielding of material between adjacent channels during ejection of implant pellets from the implant magazine under minimal force conditions. In contrast thereto, when conventional closed chambers are used to contain the implant pellets, substantial force is required to increase the size of the closed chambers since the hoop stress in the material completely surrounding the chamber must be increased substantially. If the required force is to be supplied by the implant pellets themselves interacting with the chamber walls during ejection, frangible pellets can easily be broken or crushed because of the large forces involved. With open channels substantially less force is required to enlarge the channels and that force can be provided by the interaction of the pellets and the channel walls without crushing or breaking the implant pellets. Alternatively, other means for spreading the open channels during ejection of pellets can be provided. For example, means, such as an enlarged end portion, can be provided on implant rod 38 to contact the walls of the channels defined by chambers 103 and slots 104 and increase the channel size when the implant rod 38 is forced through the channels.

The open channels also are advantageous in that they provide means for visual inspection of the pellets within the implant magazine 100 to determine that pellet-containing stations 102 contain a full pellet charge. That feature of the invention also permits visual inspection of the pellet-containing station 102, which is aligned with implant rod 38 when implant magazine 110 is loaded in injection device 10, through an inspection slot 93 in the bottom of ejector cradle 51, as seen in FIG. 9, and inspection slot 94 in the bottom of intermediate portion 18 of housing 12, as seen in FIG. 8. The visual inspection feature is particularly advantageous when partially used implant magazines having one or more expended pellet-containing stations 102 are used in the injection device 10 to ensure that a loaded pellet-containing station 102 is aligned with implant rod 38.

Figure 11A:
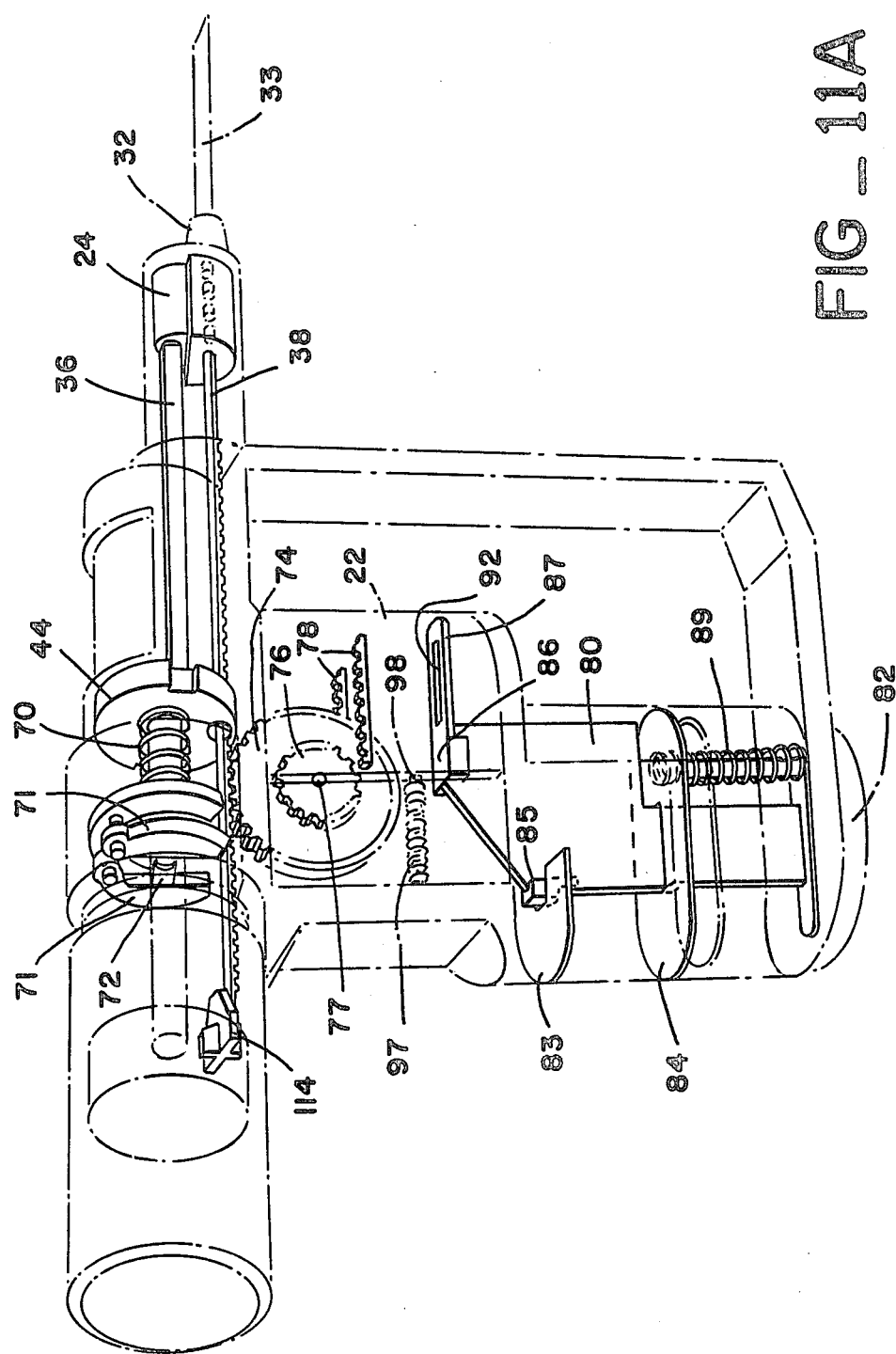

The sequence through which the implanting device progresses during the implanting operation can best be seen with reference to FIGS. 2 and 11A-11F. The configuration of the implanting instrument 10 as shown in FIGS. 2 and 11A is in its cocked, safety-on position. Prior to the actuation of the safety mechanism associated with the implant device 10, inadvertent expulsion of pellets from the implant device 10 is prevented. The safety mechanism is provided substantially by a safety plate 80 mounted within hand grip 20 which cooperates in a manner hereinafter described with trigger 22 to prevent its rearward movement until an operator is ready to proceed with the actual implanting of an animal.

With particular reference to FIG. 11A, the safety mechanism comprises a safety plate 80 retained in grip 20 between an upper bulkhead 83 and a lower bulkhead 84 formed within grip 20. Safety plate 80 is of a generally planar configuration and has formed thereon a stop member or safety catch 85 and a trigger catch 86 formed at the upper surface thereof. Safety plate 80 is restrained slideably within a slot 90 (as can best be seen in FIG. 11B) for upward and downward movement therein. A safety button or panel 82 is mounted within the lower end of grip 20 and is operable to engage safety plate 80. Trigger catch 86 forms a stop surface which engages trigger ribs 87 when the safety mechanism is on. Ribs 87 form a slot 92 which can accommodate at a later stage the width of safety plate 80 for subsequent rearward movement of trigger 22. A spring 89 is provided between lower bulkhead 84 and the bottom surface of safety plate 80 to bias it in a downward, safety-on position. When the safety mechanism is on, safety catch 85 is restrained within slot 91 formed in upper bulkhead 83 and provide a stop surface such that safety plate 80 cannot move rearwardly therein. Likewise, trigger catch 86 is engaged with the ends of ribs 87 formed on trigger 22, thus preventing rearward movement of trigger 22.

Figure 11B:
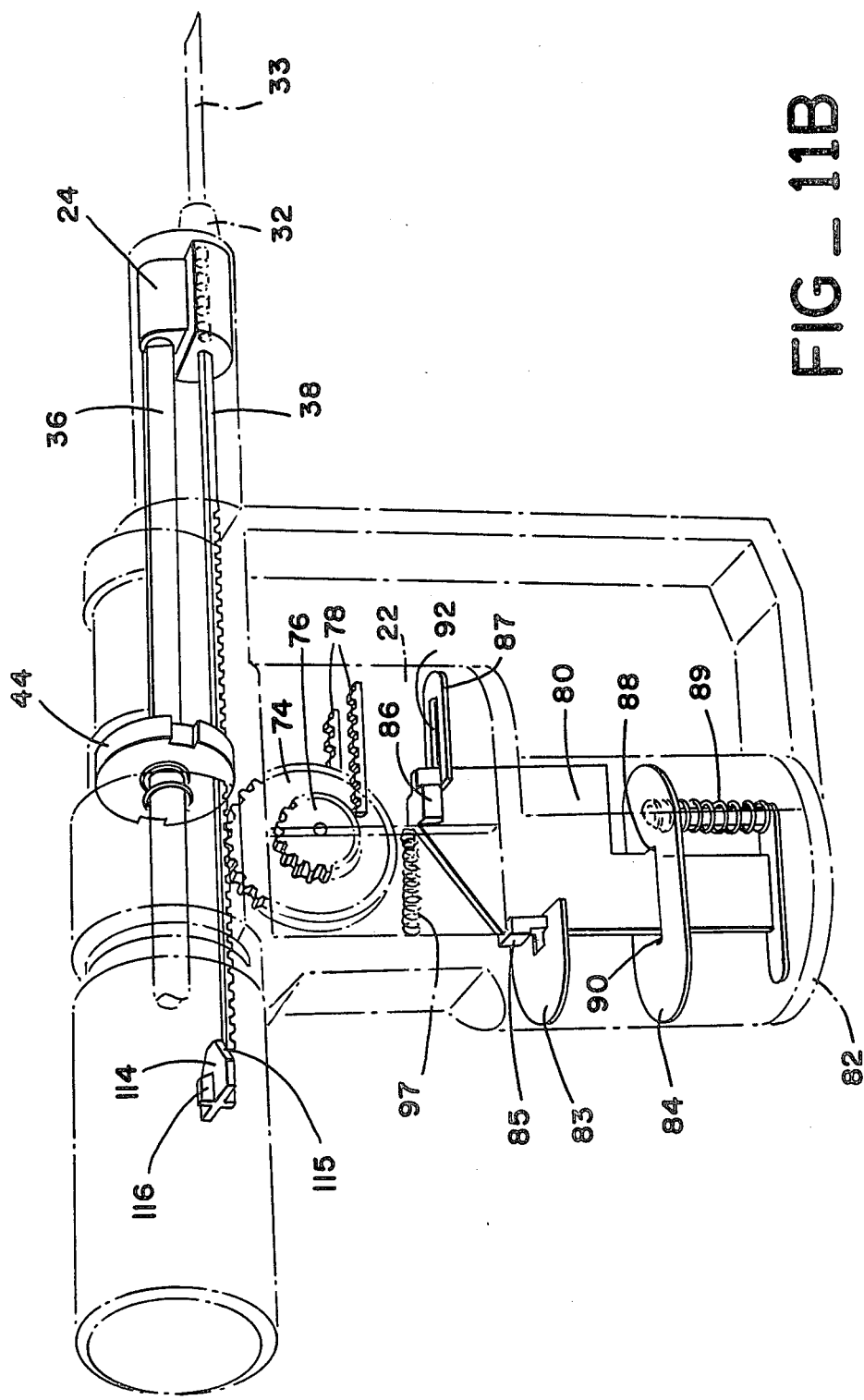

Release of the safety mechanism is shown particularly in FIG. 11B. In that configuration, safety button 82 has been moved upwardly against safety plate 80 compressing spring 89 and forcing safety plate 80 upwardly in slot 90 of lower bulkhead 84 such that safety catch 85 is moved upwardly in slot 91 formed in upper bulkhead 83. At the same time, safety off catch 88, provided by an extended surface on safety plate 80, rises above slot 90 and lower bulkhead 84 and engages the upper surface of lower bulkhead 84, thus preventing subsequent downward movement of safety 80, and trigger catch 86 has moved upwardly out of engagement with ribs 87 formed on trigger 22. A slight gap is provided below trigger catch 86 and the top of ribs 87. Accordingly, trigger 22 can now be compressed rearwardly relative to grip 20 to actuate the implanting mechanism. During that motion, slot 92 provided between ribs 87 on trigger 22 slideably receives safety plate 80. Rearward movement of trigger 22 takes place against the force of a spring 97 interposed over a post 98 formed on trigger 22 and connected between the back surface of grip 20. Spring 97 also functions to return trigger 22 to its original position after the implanting operation has been completed.

When implant device 10 is in its cocked or ready-to-fire configuration, bridge 24 is located within the forward portion 14 of housing 12 adjacent the forwardmost end thereof, and needle support 32 supports a needle 33 connected thereto in an extended position whereat the needle can be implanted under the skin of an animal. At that stage of the operational sequence of the implant device, pellets already have been moved from implant magazine 100 into lower bore 28 of bridge 24 and the end of implant rod 38 is positioned within lower bore 28 at the rearward end thereof. Also, as can best been seen from FIG. 11C, spring 70 is compressed between spring plate 44 and hub 68 on needle retraction rod 36. Sears 71 are in their compressed configuration behind and in contact with hub 68 to retain needle support 32 and needle 33 in its extended position. As trigger 22 is moved rearwardly, gear racks 78 on the inner surface of trigger 22 intermesh and engage with spur gear 76 to turn that gear in a clockwise direction as shown in FIG. 11C. Coincident therewith, large spur gear 74, which is engaged with rack gear 39 on the bottom surface of implant rod 38 causes implant rod 38 to move through bridge 24 to deposit the implant pellets within the inner bore of needle 33. At this stage of the sequence of operations, wing member 114 provided on the rear end of implant rod 38 has become positioned adjacent the rearward side of sears 71. Wing 114 is provided with a pair of leading edges 115 which are inclined inwardly to facilitate the subsequent spreading of sears 71 and the release of needle retraction rod 36.

Figure 11D:
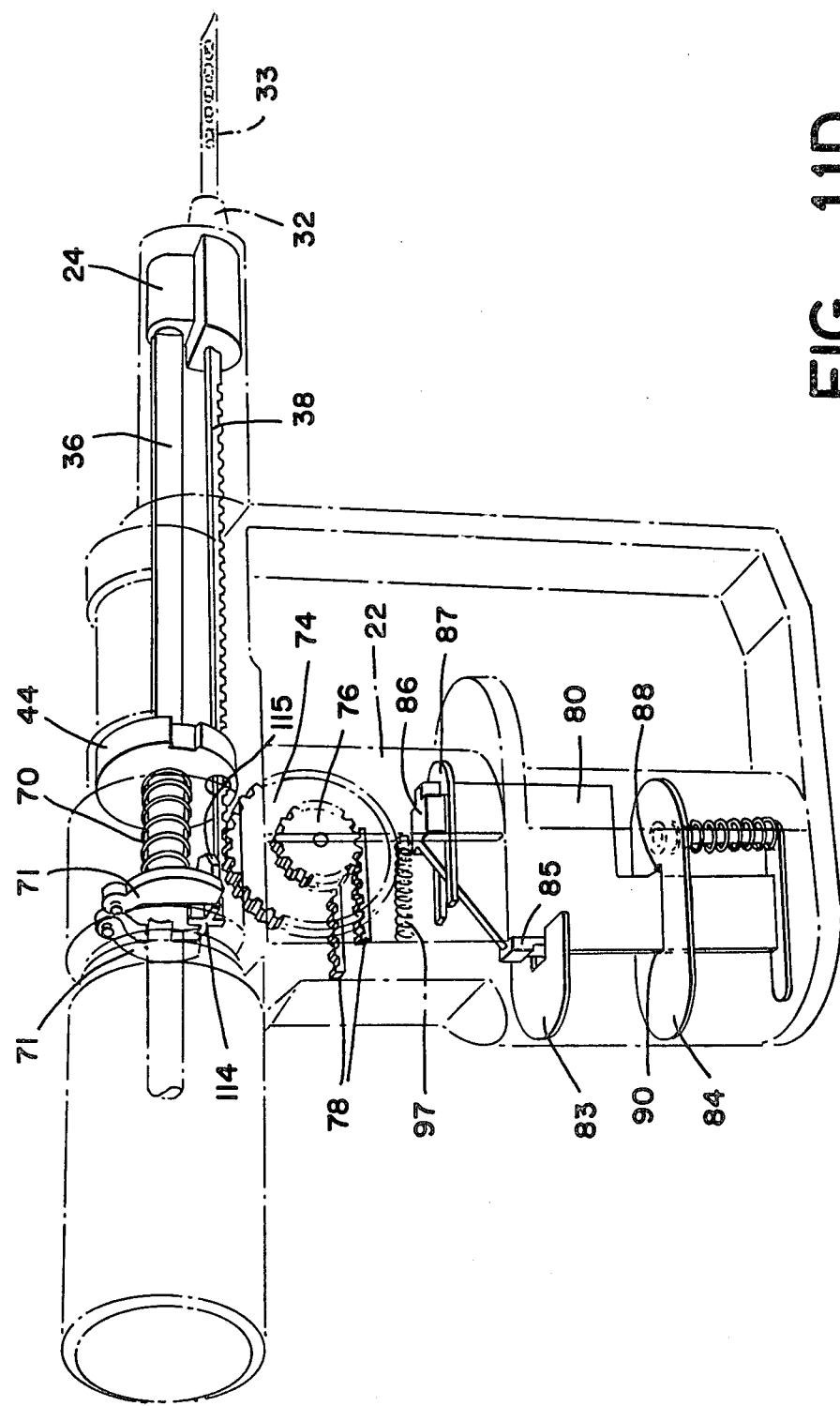

As implant rod 38 continues to move forwardly under the action of the rearward movement of trigger 22, wing 114 passes between sears 71 and spreads them apart from hub 68 on needle retraction rod 36. The particular configuration just prior to retraction of needle retraction rod 36 is shown in FIG. 11D. At that stage, trigger 22 is in its rearwardmost position and has forced implant rod 38 to its forwardmost position at which sears 71 have disengaged from hub 68 of needle retraction rod 36 and the pellets have been deposited within the bore of needle 33. At that instant, the restraining forces on needle retraction rod 36 and spring 70 are removed and spring 70 is free to propel needle retraction rod 36 in a rearward direction. Since needle retraction rod 36 cannot more axially within bridge member 24 to which is connected, the rearward movement of needle retraction rod 36 causes simultaneous movement of bridge 24 and needle support 32 and needle 33 connected thereto in a rearward fashion. However, implant rod 38 remains stationary and as the needle 33 is moved rearwardly, needle 33 is withdrawn from the animal and over implant rod 38, and the pellets remain embedded under the skin as shown most clearly in FIG. 11E. As trigger 22 moves to its rearwardmost position, the end of slot 92 contacts the front of safety plate 80 to disengage safety-off catch 88 from lower bulkhead 84. Safety plate 80 then is free to drop down through slot 90 when ribs 87 no longer contact trigger catch 86.

When bridge 24 and needle 33 have been retracted under the action of spring 70, bridge 24 assumes a position adjacent the intermediate portion 18 of housing 12 next to implant magazine 100. In that configuration, the end of implant rod 38 is located at a position adjacent the end of needle 33 which has been withdrawn to the end of housing 12.

After the needle retraction rod 36 has been moved to its rearwardmost position and the pellets have been implanted into the animal upon retraction of needle 33 about implant rod 38, release of trigger 22 by an operator permits spring 97 to force trigger 22 to its forwardmost position and return implant rod 38 through the action of gears 74, 76 and 78 to a retracted position as shown in FIG. 11F. At that position, the end of implant rod 38 is positioned through implant magazine 110 and at the rearward end of lower bore 28 formed in bridge 24. Additionally, safety plate 80 has dropped down to the safety on configuration whereat trigger catch 86 is again in engagement with ribs 87 formed on the inside of trigger 22 and safety catch 85 is in contact with upper bulkhead 83. Thus, rearward movement of trigger 22 is again prevented until safety button 82 is actuated and the sequence for the operation of the implant device is again undertaken.

The cocking sequence to prepare implanter 10 for a subsequent implant is shown particularly in FIGS. 12A–12D. A generally rectangular track 122 is formed in the outer surface of the rearward end 16 of housing 12. Restrained in track 122 is a pin 126 which is fixed to grip 55 on the inner surface thereof and is adapted to ride within track 122. Guide tube 56 is formed with a circumferential slot 124 on the outer surface thereof and an adjacent and interconnecting guide slot 128 which extends from slot 124 to the forward end of guide tube 56. As can best be seen from FIG. 12A, slot 124 is adapted to receive a guide rib 116 which is formed on the upper surface of wing 114 on implant rod 38. By rotating grip 55 in a counterclockwise direction, guide tube 56 which is attached to grip 55 is also rotated in a counterclockwise direction and slot 124 is rotated to a position as shown in FIG. 12B. At that position, guide rib 116 is picked up and retained within slot 124 for subsequent rearward movement of implant rod 38. At the same time, pin 126 has rotated in the front, vertically-extending portion of track 122 to its position as shown in FIG. 12B. That rotation of grip 55 and guide tube 56 is in a direction in which there is no engagement of clutch elements 64 and 65. Accordingly, movement from the position shown in FIG. 12A to the position shown in FIG. 12B does not rotate needle retraction rod 36, which is keyed to clutch tube 62 by the hexagonally-shaped end 66, or implant magazine 100, which is keyed to needle retraction rod 36.

At the positions shown in FIGS. 12A and 12B, implant rod 38 is extending through the spent pellet station 102 of implant magazine 100 and has its end positioned adjacent bridge 24 as was the case after the implant operation had been completed. However, as grip 55 is moved rearwardly over rearward portion 16 of housing 12, guide rib 116 is picked up by slot 124 and implant rod 38 is drawn rearwardly through and out of the spent chamber of implant magazine 100 to a position at which its end is removed from implant magazine 100 and resides adjacent spring plate 44. That rearward movement of guide tube 56 which is connected to grip 55 also moves sears 71 rearwardly over spring 70 and hub 68 of needle retraction rod 36 to a position as shown in FIG. 12C. At that position, sears 71 are again compressed by the action of spring 73 and tabs 72 are riding on the rearward portion of needle retraction rod 36. Although clutch tube 62 has not been rotated by the counterclockwise rotation of grip 55 and guide tube 56, the rearward movement of grip 55 and guide tube 56 does cause clutch tube 62 to be withdrawn over a portion of the rearward end 66 of needle retraction rod 36. However, the rearward end 66 of needle retraction rod 36 remains keyed to clutch tube 62 by means of the hexagonally-shaped end 66 and the complementary surface formed within the inner surface of clutch tube 62. At the position shown in FIG. 12C, guide pin 126 has traversed the lower longitudinal track portion of track 122 provided in housing 12. As also can be seen from FIG. 12C, the end of implant rod 38 is immediately adjacent the end of implant magazine 100, but one position removed from the loaded pellet position 102 shown in that figure.

Movement of loaded pellet position 102 into alignment with implant rod 38 is accomplished by rotating grip 55 and guide tube 56 attached thereto in a clockwise direction to the position shown in FIG. 12D. At that position, guide pin 126 has traversed the rearward, vertically extending portion of track 122. Clockwise movement of grip 55 and guide tube 56 causes slot 124 to move to a position out of engagement with guide rib 116 formed on wing 114. At the same time, clockwise rotation of grip 55 and guide tube 56 causes clutch elements 64 and 65 to interact and become engaged such that the aforementioned clockwise movement causes clutch tube 62 also to move in a clockwise direction. Since clutch tube 62 is keyed to needle retraction rod 36 by means of the hexagonal end 66 of needle retraction 36 and the complementary surface of clutch tube 62, needle retraction rod 36 also rotates in a clockwise direction. Since implant magazine 100 is supported on and engaged with needle retraction rod 36 by means of slot 110 formed in implant magazine 100, implant magazine 100 is also rotated along with needle retraction rod 36 to transport pellet-containing station 102 to a position in alignment with implant rod 38. Thus, during the cocking operation, implant magazine 100 has been automatically indexed to the next implant position for subsequent implanting of the pellets contained within station 102 into an animal.

The subsequent movement of cocking grip 55 forwardly along rearward portion 16 of housing 12 forces guide tube 56 in the forward direction also. That movement causes a corresponding movement of implant rod 38 forwardly through implant magazine 100, forcing the pellets to spread chamber 103 and slot 104 by their interaction with ramps 108, to deposit pellets within pellet containing station 102 into bridge 24 which is located immediately adjacent the forward end of implant cartridge 100. That movement of implant rod 38 is caused by the engagement of guide rib 116 with the end of slot 128 formed in the outer surface of guide tube 56. At the same time, forward movement of grip 55 and guide tube 56 forces sears 71 along rod 36 to a position adjacent hub 68. At that position, tabs 72 of sears 71 engage the rearward surface of hub 68 and begin to force needle retraction rod forwardly and compress spring 70 which is restrained between hub 68 and spring plate 44. Since needle retraction rod 36 cannot move axially within bridge 24, forward movement of needle retraction rod 36 caused by the action of sears 71 upon hub 68 also forces bridge 24 forwardly in the forward portion 14 of housing 12 to assume the configuration as shown in FIG. 11A. In that configuration, needle 33 supported on needle support 32 has again become extended outwardly from the front surface of housing 12. When grip 55 has been moved to its forwardmost position at which pin 126 has traversed the upper longitudinal portion of track 122, the implant instrument has assumed a configuration as is shown in FIG. 11A. Track 122 is conveniently provided with a set of ratchet teeth (not shown) which prevents the rearward movement of grip 55 under the action of spring 70 which is pressing on hub 68 of needle retraction rod 36. However, that ratchet mechanism does not prevent the rearward movement of needle retraction rod 36 under the action of spring 70 during the actual implant operation when sears 71 are spread and disengaged from hub 68 since needle retraction rod 36 is free to move axially within clutch tube 62. Thus, rearward motion of needle retraction rod 36 within clutch tube 62 does not impart any motion to grip 55 against the action of ratchet teeth formed in track 122.

In another aspect of this invention, indexing means are provided on implant rod 38 and large spur gear 74 to ensure that implant rod 38 is in an appropriate position extending outwardly of needle 33 when needle 33 is retracted about implant rod 38 to effect positive implantation of pellets within an animal. That indexing means is provided by a large gear tooth 130 on implant rod 38 which engages a corresponding recess 131 formed in large spur gear 74. During the manufacture of the implant device, implant rod 38 is aligned with spur gear 74 such that tooth 130 rests within recess 131. Tooth 130 is appropriately positioned with respect to the end of implant rod 38 such that when implant rod 38 is forced through bridge 24 and into needle 33, subsequent retraction of needle 33 about implant rod 38 results in the end of rod 38 being positioned immediately adjacent the retracted end of needle 33. Additionally, tooth 130 on implant rod 38 cooperates with slots 104 in implant magazine 100 to provide a guiding and stabilization means to effect proper ejection of pellets from implant stations 102 without breaking or crushing of the pellets. As tooth 130 passes through slots 104, tooth 130 provides a stabilization mechanism as implant rod 38 moves through implant magazine 100 and is withdrawn rearwardly therefrom, which prevents implant rod 38 from becoming skewed within implant cartridge 100. There is no tendency for implant rod 38 to hang up within implant magazine 100 during the withdrawal of implant rod 38 therefrom. Thus, not only is implant magazine 100 stabilized by the action of nubs 52 on ejector cradle 51 in corresponding slots 104 of the implant magazine, but it is stabilized by the action of tooth 130 as it passes through the slot 104 which contains the particular pellet charge to be implanted.

While the invention has been described with reference to the specific embodiments thereof, it should be understood by those skilled in the art that various changes can be made and equivalents may be substituted therefor without departing from the true spirit and scope of the invention. All such modifications are intended to be within the scope of the claims appended hereto.

What is claimed is:

1. A device for implanting pellets and the like into an animal comprising:

(a) a housing having a forward end and a rearward end;

(b) needle support means mounted on said housing adjacent the forward end thereof, said needle support means being moveable between a first position and a second position;

(c) means on said housing for supporting an implant magazine having a plurality of pellet-containing stations therein;

(d) an implant rod supported within said housing and moveable between a third position and a fourth position;

(e) first means for moving said implant rod between said third and fourth positions;

(f) a needle retraction rod supported on said housing, said needle retraction rod being coupled to said needle support means and adapted to engage an implant magazine supported on said housing;

(g) means on said housing for rotating said needle retraction rod to align a pellet containing station of an implant magazine with said implant rod; and (h) second means for moving said needle support means between said first and second positions.

2. The device of claim 1 including means associated with said housing for ejecting an implant magazine from said support means on said housing.

3. The device of claim 2 wherein said ejection means includes a support cradle for an implant magazine, said support cradle having first biasing means associated therewith for biasing an implant magazine outwardly from said housing.

4. The device of claim 3 wherein said first biasing means is a spring.

5. The device of claim 1 including third means on said housing for releaseably maintaining said needle support means in said first position.

6. The device of claim 5 wherein said third means includes at least one releaseable stop on said housing engageable with a portion of said needle retraction rod.

7. The device of claim 6 including fourth means on said implant rod for releasing said stop from engagement with said portion of said needle retraction rod.

8. The device of claim 1 wherein said rotating means includes a one-way clutch operatively engageable with said needle retraction rod.

9. The device of claim 8 wherein said one-way clutch is a fiber clutch.

10. The device of claim 8 wherein said one-way clutch is a wrapped-spring clutch.

11. The device of claim 1 wherein said second means includes second biasing means for biasing said needle retraction rod toward the rearward end of said housing.

12. The device of claim 11 wherein said second biasing means is a spring.

13. The device of claim 1 including safety means associated with said housing for releaseably maintaining said implant rod in said third position.

14. The device of claim 1 wherein said first means includes trigger means supported on said housing and means operatively coupling said trigger means and said implant rod.

15. The device of claim 14 wherein said coupling means includes a first rack gear on said trigger means, a first spur gear engaging said first rack gear, the second rack gear on said implant rod and a second spur gear integrally joined with said first spur gear and engaged with said second rack gear.

16. The device of claim 15 wherein said second rack gear and said second spur gear include indexing means thereon.

17. The device of claim 16 wherein said indexing means includes an enlarged tooth on said second rack gear and a complementary recess on said second spur gear for engagement therewith.

18. The device of claim 17 including, in combination, an implant magazine supported in said housing, said implant magazine having guide means thereon for receiving said enlarged tooth.

19. The device of claim 18 wherein said guide means includes a longitudinal slot in each of said pellet containing stations of said implant magazine.

20. The device of claim 14 including safety means associated with said housing and said trigger means, said safety means including a stop surface for releaseably engaging said trigger means to prevent rearward movement thereof.

21. The device of claim 20 including a handle depending from said housing, said safety means including a plate supported within said handle, said plate having a first surface thereon for engaging a first portion of said handle and a second surface thereon for releaseably engaging a portion of said trigger means.

22. The device of claim 21 wherein said plate has a third surface thereof for releaseably engaging a second portion of said handle to maintain said second surface released from engagement with said trigger means when said third surface is engaged with said second portion of said handle.

* * * * *